(12) United States Patent
Zinn

(10) Patent No.: US 8,591,483 B2
(45) Date of Patent: Nov. 26, 2013

(54) MULTI-PORT ASSEMBLY

(75) Inventor: Kenneth M. Zinn, Westport, CT (US)

(73) Assignee: Medical Components, Inc., Harleysville, PA (US)

( * ) Notice: Subject to any disclaimer, the term of this patent is extended or adjusted under 35 U.S.C. 154(b) by 116 days.

(21) Appl. No.: 12/908,925

(22) Filed: Oct. 21, 2010

(65) Prior Publication Data

US 2011/0098662 A1 Apr. 28, 2011

Related U.S. Application Data

(60) Provisional application No. 61/255,148, filed on Oct. 27, 2009.

(51) Int. Cl.
*A61M 37/00* (2006.01)
(52) U.S. Cl.
USPC .................................................. 604/288.01
(58) Field of Classification Search
USPC ................ 604/288.01–288.04, 174, 175
See application file for complete search history.

(56) References Cited

U.S. PATENT DOCUMENTS

| 4,170,082 | A | 10/1979 | Freedman | |
|---|---|---|---|---|
| 4,692,146 | A * | 9/1987 | Hilger | 604/288.01 |
| 5,360,407 | A | 11/1994 | Leonard | |
| 5,387,192 | A | 2/1995 | Glantz et al. | |
| 5,433,314 | A | 7/1995 | Lin | |
| 5,445,616 | A | 8/1995 | Kratoska et al. | |
| 5,718,682 | A * | 2/1998 | Tucker | 604/288.02 |
| 8,343,115 | B2 * | 1/2013 | Lynch et al. | 604/288.03 |
| 2004/0133173 | A1 | 7/2004 | Edoga et al. | |
| 2004/0199129 | A1 | 10/2004 | DiMatteo | |
| 2006/0116648 | A1 * | 6/2006 | Hamatake | 604/288.02 |
| 2009/0118683 | A1 * | 5/2009 | Hanson et al. | 604/288.01 |
| 2009/0254052 | A1 * | 10/2009 | Birk et al. | 604/288.01 |

OTHER PUBLICATIONS

International Search Report and Written Opinion; International Application No. PCT/US2010/053462; International Filing Date: Oct. 21, 2010; 8 pages.

* cited by examiner

*Primary Examiner* — Kami A Bosworth
(74) *Attorney, Agent, or Firm* — Blank Rome LLP

(57) ABSTRACT

A multi-port assembly includes a base with a surface, a port receiving area on the surface, and a port coupling connected to the base. The port receiving area is adapted to receive a mating surface of a port, and the port coupling is adapted to mate the port to the port receiving area.

20 Claims, 9 Drawing Sheets

US 8,591,483 B2

MULTI-PORT ASSEMBLY

RELATED APPLICATION

The present invention claim priority to U.S. Provisional Patent Application No. 61/255,148, filed on Oct. 27, 2010. The disclosure of which is incorporated herein by reference in its entirety in this application.

FIELD OF THE INVENTION

The present invention relates to subcutaneous implantable ports. In particular, the present invention relates to an assembly that can receive multiple subcutaneous implantable ports.

BACKGROUND OF THE INVENTION

Vascular access devices such as subcutaneous implantable ports are often inserted inside a major vein for a period of months or years so that blood can be repeatedly drawn or medication and nutrients can be injected into the patient's bloodstream on a regular basis. Subcutaneous implantable ports, which are also sometimes referred to as subcutaneous access ports, may be used for giving chemotherapy, providing blood transfusions, taking blood samples, delivering intravenous (IV) fluids, providing IV medicines, and the like. Known ports have an attached catheter which is typically a soft tube that is implanted into a patient's blood vessel.

However, sometimes there is a medical need to have more than one port chamber to access for a dedicated use. Hence, there is a need for an assembly that combines ports such that the assembly can provide multiple ports in a single assembly.

SUMMARY OF THE INVENTION

Accordingly, one aspect of the invention may provide a multi-port assembly. The multi-port assembly includes a base with a surface, a port receiving area on the surface, and a port coupling connected to the base. The port receiving area is adapted to receive a mating surface of a port, and the port coupling is adapted to mate the port to the port receiving area.

Another aspect of the invention may provide a multi-port assembly. The multi-port assembly includes a base with a surface, port receiving areas on the surface, and port couplings connected to the base and along a periphery of at least one of the port receiving areas. Each port receiving area is adapted to receive a mating surface of a port. Each port coupling is adapted to mate the port to one of the port receiving areas.

Other objects, advantages and salient features of the invention will become apparent from the following detailed description, which, taken in conjunction with the annexed drawings, discloses exemplary embodiments of the present invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 5:
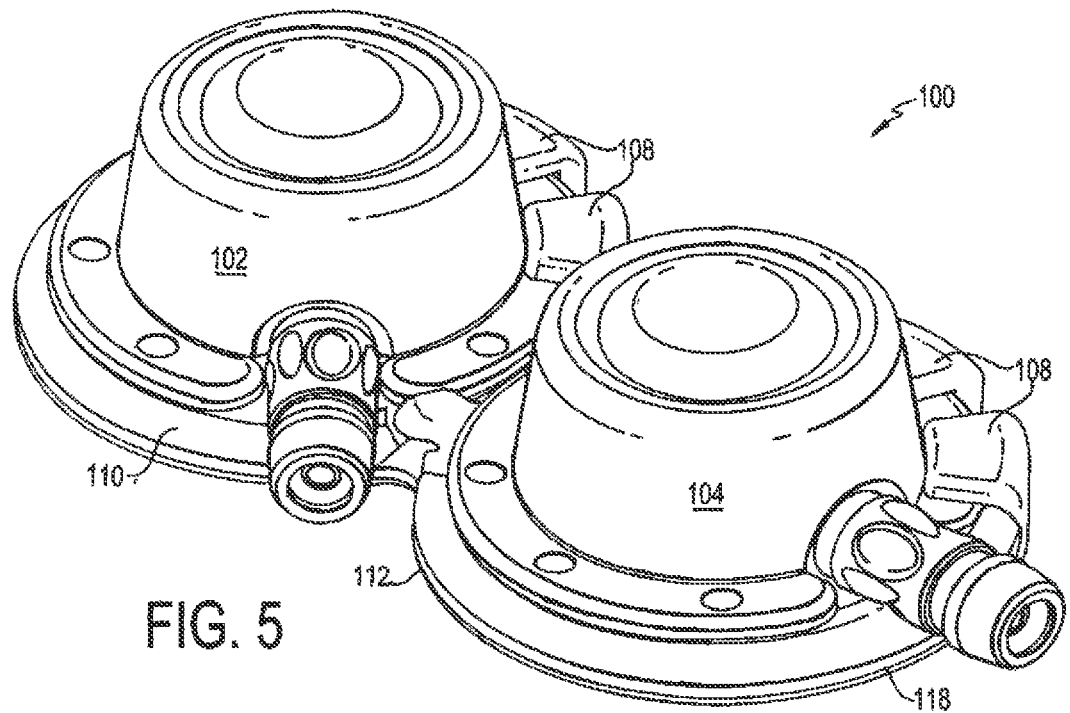
FIG. 5 is a perspective view of the multi-port assembly shown in FIG. 1 with ports.
Figure 6:
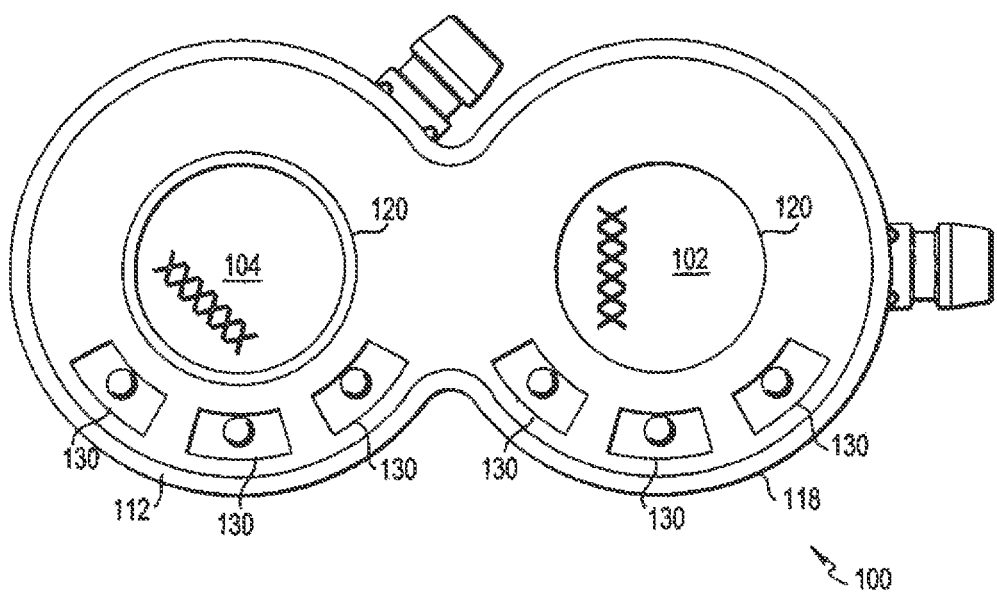
FIG. 6 is an underside plan view of the multi-port assembly shown in FIG. 5.

Referring to FIGS. 1-20, the present invention provides a multi-port assembly 100 that can receive one or more ports 102 and 104 (shown in FIGS. 5-6) and form a single assembly 100. The multi-port assembly 100 includes a base 106 and one or more port couplings 108 coupled to the base 106.

Turning to FIGS. 1-6, the base 106 provides mechanical support for the one or more ports 102 and 104. The base 106 can include, at least, a first surface 110 and a second surface 112 opposite the first surface 110. Because the base 106 receives one or more ports 102 and 104, the base 106 can have one or more port receiving areas 114 and 116, whereby each port receiving area 114 or 116 receives a respective port 102 or 104. Each port receiving area 114 and 116 may be shaped to correspond to a mating surface of the port 102 or 104 that is received in the port receiving area 114 or 116. The port receiving areas 114 and 116 may be disposed next to each other on a surface 110 or 112 of the base 106. Alternatively, in other embodiments, one port receiving area 114 may be on the first surface 110, and another port receiving area 116 may be on the second surface 112. Furthermore, each port receiving area 114 and 116 can be substantially flush with one of the surfaces 110 or 112 of the base 106, or in alternate embodiments, one or more of the port receiving areas 114 or 116 can be disposed above and parallel to one of the surfaces 110 or 112 of the base 106. At least one of the port receiving areas 114 or 116 can be disposed to compensate for different heights of the ports 102 and 104 such that the ports 102 and 104 reach generally the same height above the base 106. In other embodiments, at least one of the port receiving areas 114 or 116 may be disposed such that the ports 102 or 104 are at different heights above the base 106.

In the embodiment shown in FIGS. 1-6, the base 106 includes two port receiving areas 114 and 116. However, the number of port receiving areas 114 and 116 is not meant to be limiting. In other embodiments, the base 106 can have more or less than the two port receiving areas 114 and 116 shown. The number of port receiving areas 114 and 116 is determined, for example, by the number of ports 102 and 104 required to administer the desired fluids such as chemotherapy, blood products, IV fluids, medicines and the like.

The base 106 can have a generally planar shape. As shown in the figures, the first surface 110 and the second surface 112 are disposed substantially parallel to each other. In other embodiments, the base 106 may be contoured to substantially match the contour of the space created under the skin for the multi-port assembly 100, sometimes referred to as a subcutaneous port pocket. Also, the periphery 118 of the base 106 can substantially match a periphery of one or more of the ports 102 and 104. In the embodiment shown, the portion of the ports 104 and 116 received by the base 106 may have a circular periphery, and thus, the base 106 has a periphery 118 that substantially resembles a figure eight. However, in other embodiments, the base 106 can have any suitable shape to receive the ports 102 and 104, to be disposed in the port pocket, to match the incision at the entrance of the port pocket, combinations of the aforementioned, or some other criteria.

The base 106 can have a bore 120. The bore 120 minimizes the material used for the base 106, minimizes surface areas that may potentially become infected or form clots, or provides a visual pathway to the mating surface of the port 102 or 104. The bore 120 can have any suitable shape. In the embodiment shown, the base 106 can have a substantially circular bore 120 in the center of one or more of the port receiving areas 114 and 116. In other embodiments, the bore 120 may be generally elliptical, triangular, trapezoidal, some other polygonal shape, combinations of the aforementioned, or some other suitable shape. The bore 120 can extend through the port receiving area 114 and 116, one or more of the surfaces 110 or 112 of the base 106, and the base 106.

The base 106 can be made from plastics, metals such as titanium, alloys such as stainless steel, rubber, synthetic rubber, glass, ceramic, combinations of the aforementioned, or some other suitable material. Suitable plastics can include biocompatible, medical grade polysulfone, polyurethane, thermoset, thermoset polyethylene, liquid crystal polymers, thermoplastic such as acrylic, thermoplastic polymer such as polycarbonate, thermoplastic fluoropolymer, fluorocarbon-based polymer, polyvinylidene fluoride, ethylene tetrafluoroethylene, polyaryletherketone, and the like. The base 106 may be made of one material with a coating or plating of another material. The base 106 may be of substantially solid construction or include one or more hollows. The base 106 may be substantially rigid such that the base 106 retains its shape or flexible such that the base 106 can generally conform to a surface within the port pocket.

One or more port couplings 108 are coupled to the base 106. The one or more port couplings 108 couple a port 102 or 104 to the base 106. The port coupling 108 can be a mechanical coupling such as an interlocking insert and slot, mating threads, pressure fitting, friction fitting, snaps, clasps, hooks, some other mating or interlocking mechanical structures, rivets, welds, bolts, screws, combinations of the aforementioned, or some other mechanical coupling. In other embodiments, the port coupling 108 can include a chemical coupling such as an adhesive, glue, or some other suitable chemical coupling.

Figure 4:
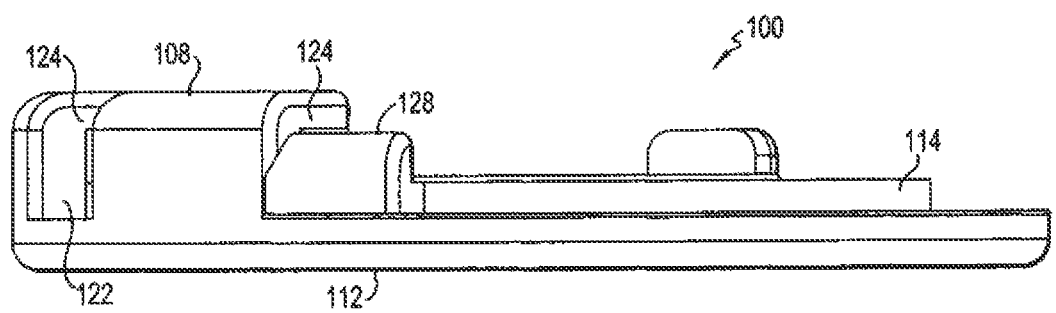
FIG. 4 is a side elevational view of the multi-port assembly shown in FIG. 1.

As best seen in the embodiment shown in FIG. 4, the port coupling 108 includes an extending portion 122 that extends from the base 106 and a coupling portion 124 that is disposed at an end of the extending portion 122. The extending portion 122 can be substantially perpendicular to the first surface 110 of the base 106, and the coupling portion 124 can extend generally perpendicular to the extending portion 122 such that the coupling portion 124 is substantially parallel to the first surface 110 of the base 106. The extending portion 122 can be sized so that the extending portion 122 generally corresponds to the thickness of a flange of the port 102 or 104.

Figure 3:
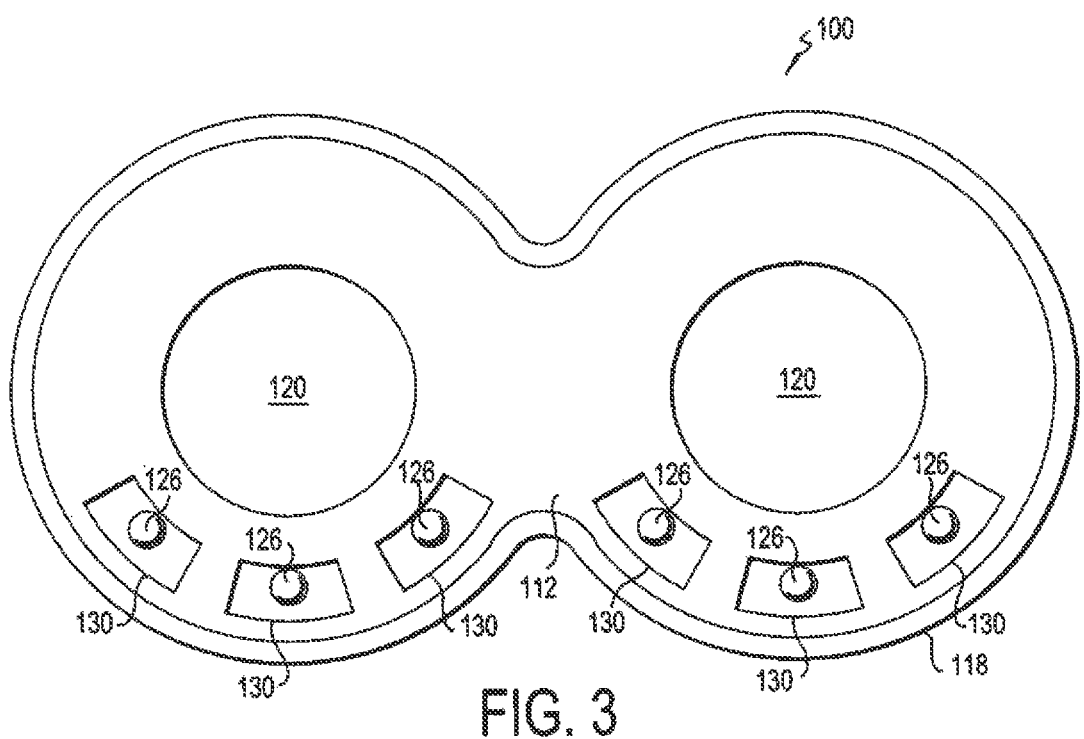
FIG. 3 is an underside plan view of the multi-port assembly shown in FIG. 1.

Also, the coupling portion 124 can include a peg 126 that engages a surface of the port 102 or 104, as best shown in FIG. 3. The peg 126 can have the generally hemispherical shape as shown or some other suitable shape that can touch, press, snare, hook, or otherwise engage the port 102 or 104. The coupling portion 124 can also have more than the one peg 126 shown. The exact number of pegs 126 may be depend on, for example, the anticipated mechanical force required to mate the port 102 or 104 to the port coupling 108.

As shown in FIG. 3, the base 106 can have one or more apertures 130. The one or more apertures 130 minimizes the material used for the base 106, minimizes surface areas that may potentially become infected or form clots, or provides a visual pathway to the mating surface of the port 102 or 104. The one or more apertures 130 can have any suitable shape. In the embodiment shown, the apertures 130 are disposed under the coupling portions 124 of the port couplings 108.

Figure 1:
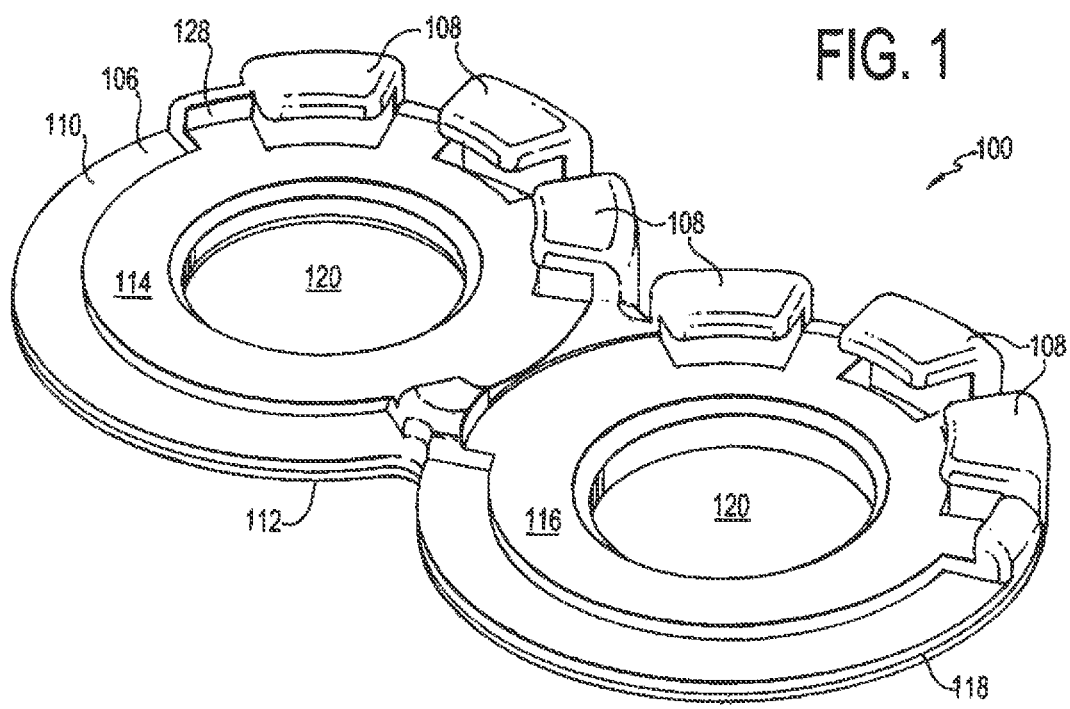
FIG. 1 is a perspective view of a multi-port assembly without ports in accordance with an embodiment of the invention.
Figure 2:
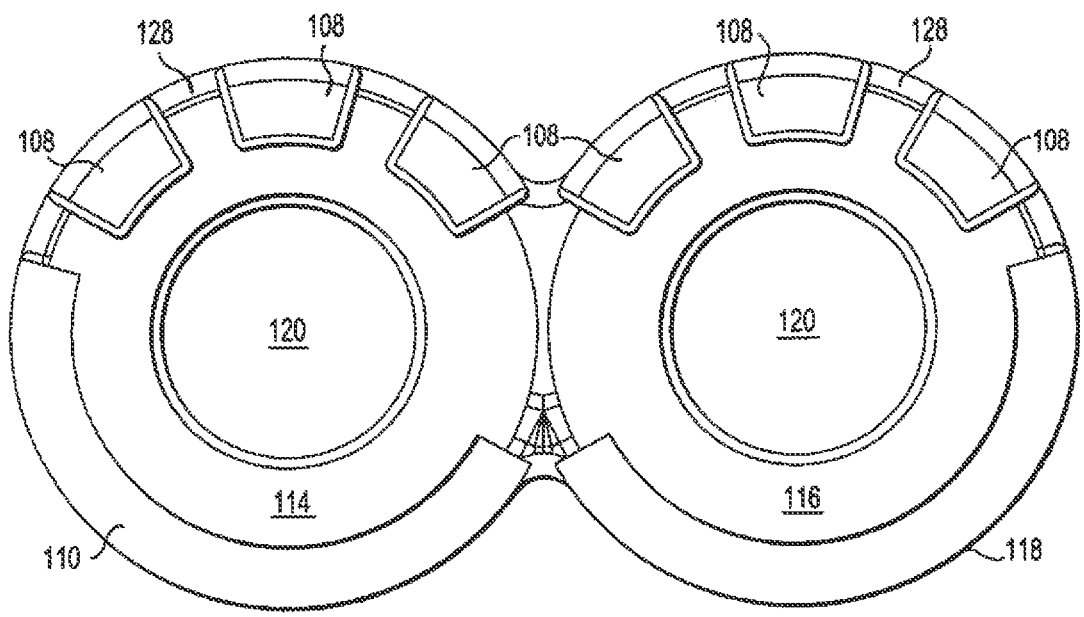
FIG. 2 is an overhead plan view of the multi-port assembly shown in FIG. 1.

The one or more port couplings 108 may be disposed on a flange 128, as shown in FIGS. 1, 2, and 4. The flange 128 can provide mechanical support to one or more of the port couplings 108. Also, as best shown in FIGS. 1 and 2, the flange 128 can provide mechanical support to a periphery of each of the ports 102 and 104. The flange 128 can extend along, at least, a portion of the periphery 118 of the base 106. The flange 128 can join one, most, or all of the port couplings 108. In the embodiment shown, the flange 128 extends around approximately one-third of the periphery of each port receiving area 114 and 116.

Figure 7:
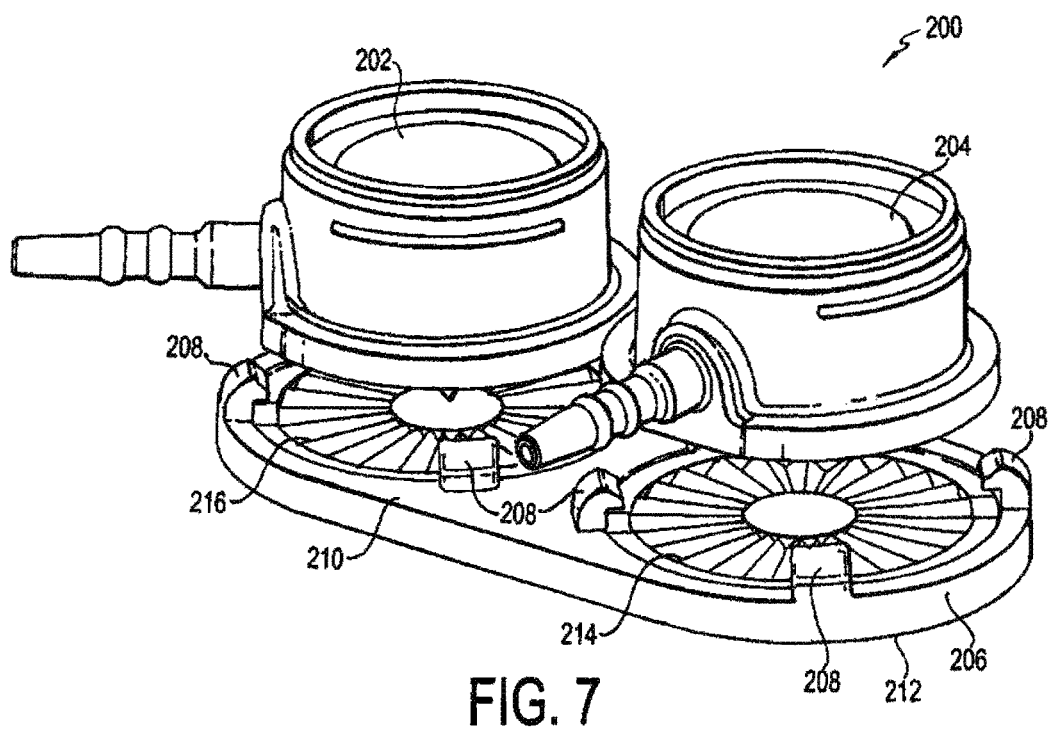
FIG. 7 is an exploded perspective view of a multi-port assembly in accordance with another embodiment of the invention.

Referring to FIGS. 7-10, another embodiment of the multi-port assembly 200 is shown. The multi-port assembly 200 can receive one or more ports 202 and 204, which have a different outer shape than ports 102 and 104. The multi-port assembly 200 has a base 206 and ports couplings 208 coupled to the base 206. The base 206 includes, at least a first surface 210 and a second surface 212 that are substantially similar to the first surface 110 and the second surface 112 of the multi-port assembly 100, thus a detailed description thereof is omitted. The base 206 can include one or more port receiving areas 214 and 216. The port receiving areas 214 and 216 are substantially similar to the port receiving areas 114 and 116 of the multi-port assembly 100; however, as shown in FIG. 7, one or more of the port receiving areas 214 and 216 can have a knurled or ridged surface.

Figure 8:
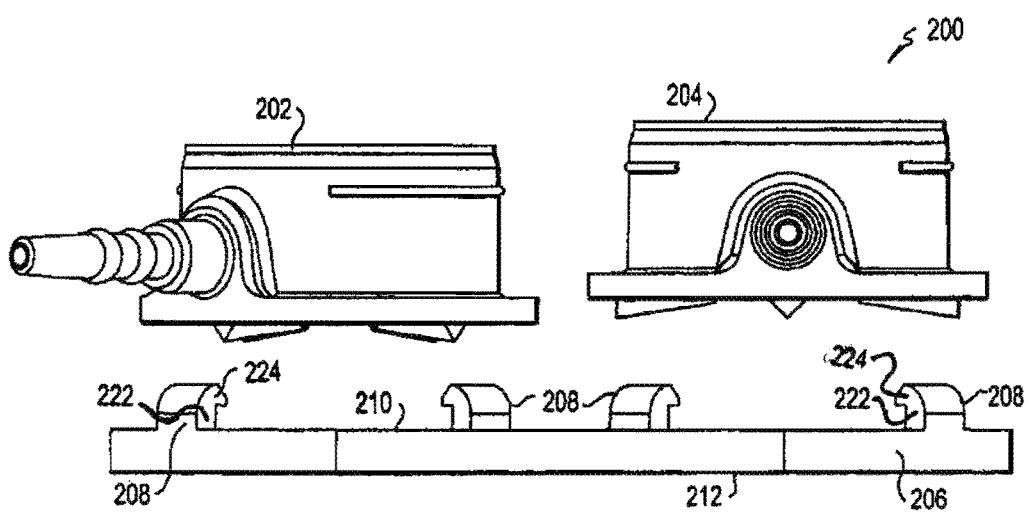
FIG. 8 is an exploded front elevational view of the multi-port assembly shown in FIG. 7.
Figure 9:
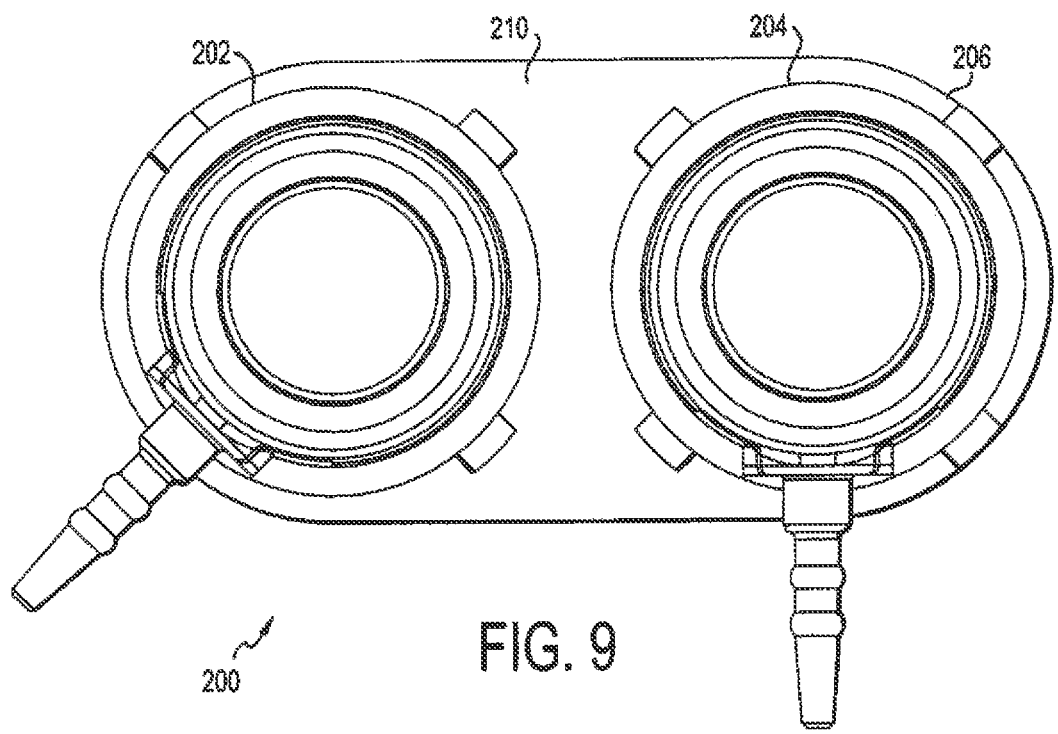
FIG. 9 is an overhead plan view of the multi-port assembly shown in FIG. 7.
Figure 10:
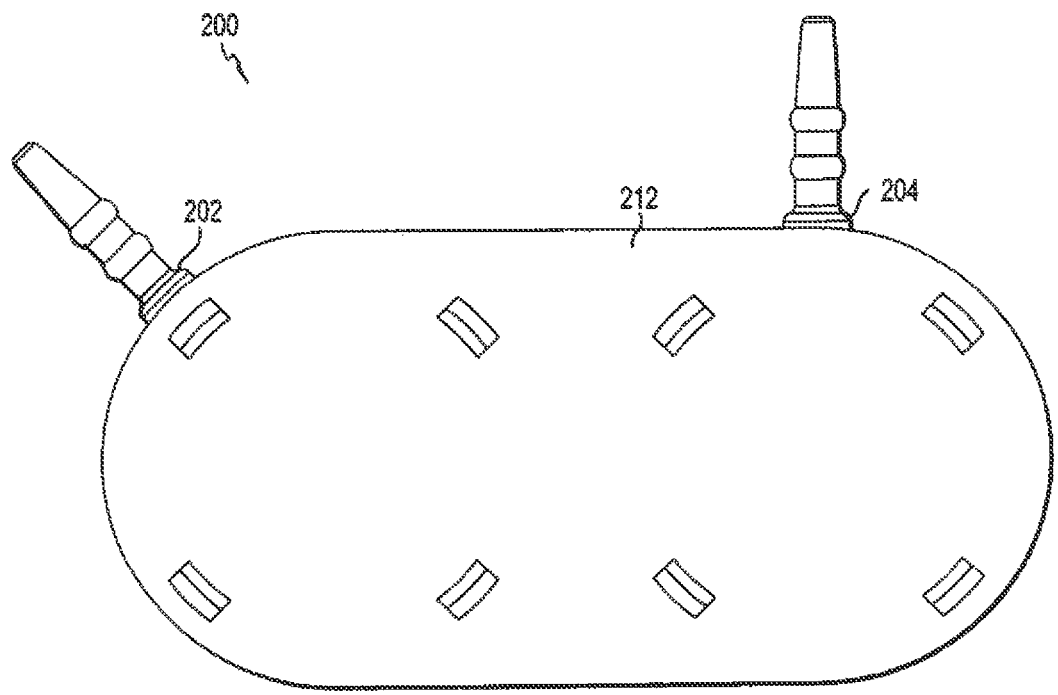
FIG. 10 is an underside plan view of the multi-port assembly shown in FIG. 7.
Figure 11:
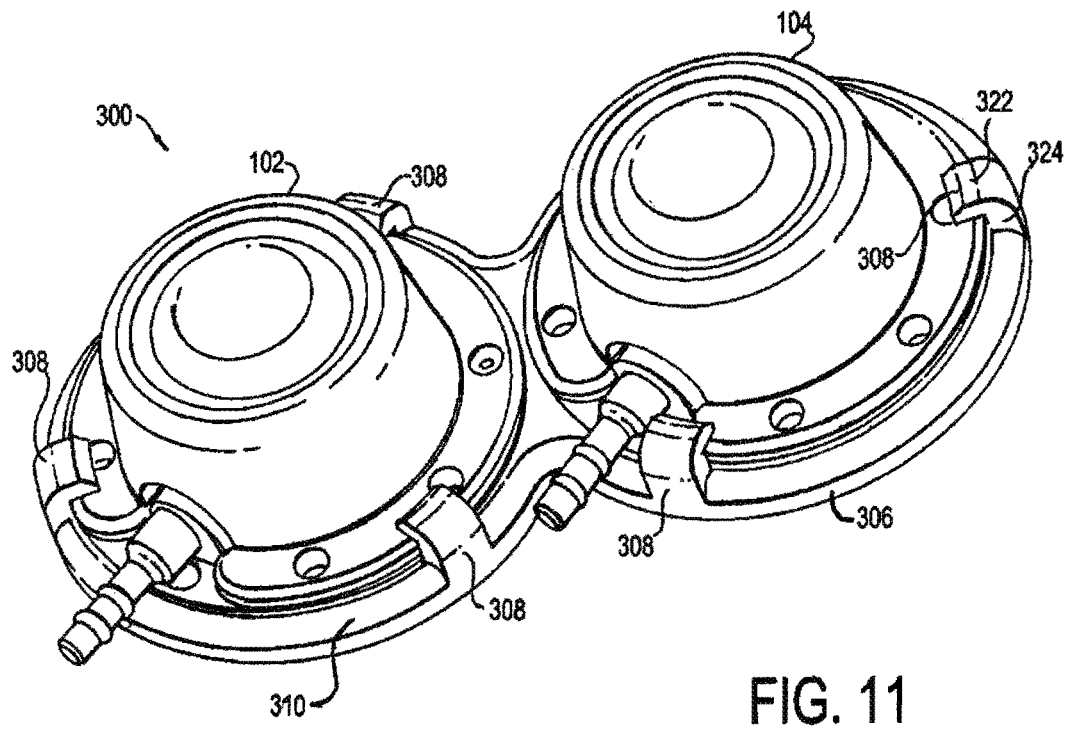
FIG. 11 is a perspective view of a multi-port assembly in accordance with yet another embodiment of the invention.
Figure 12:
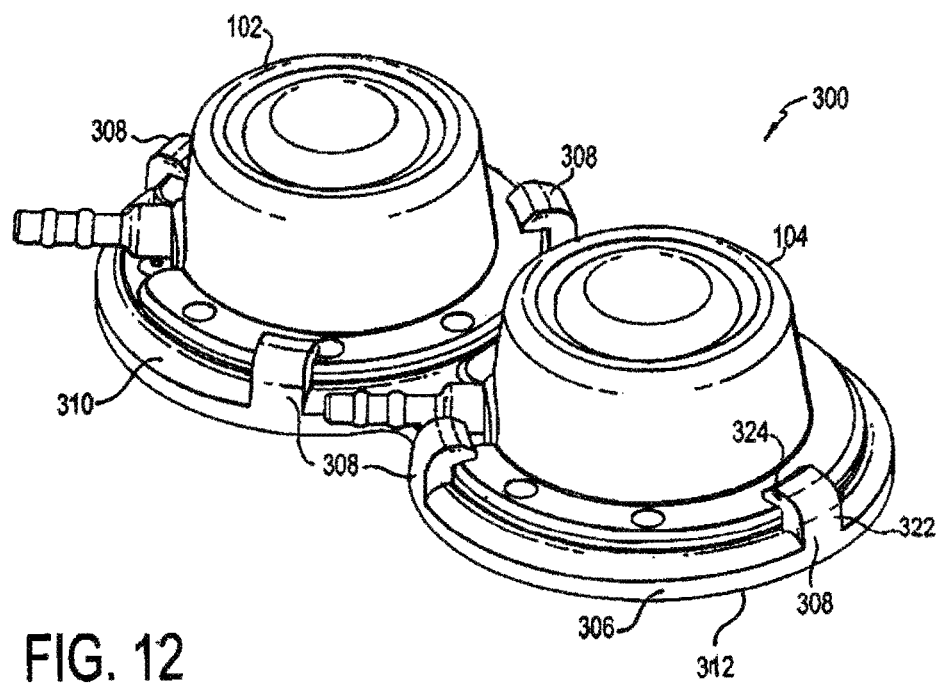
FIG. 12 is another perspective view of a multi-port assembly shown in FIG. 11.
Figure 13:
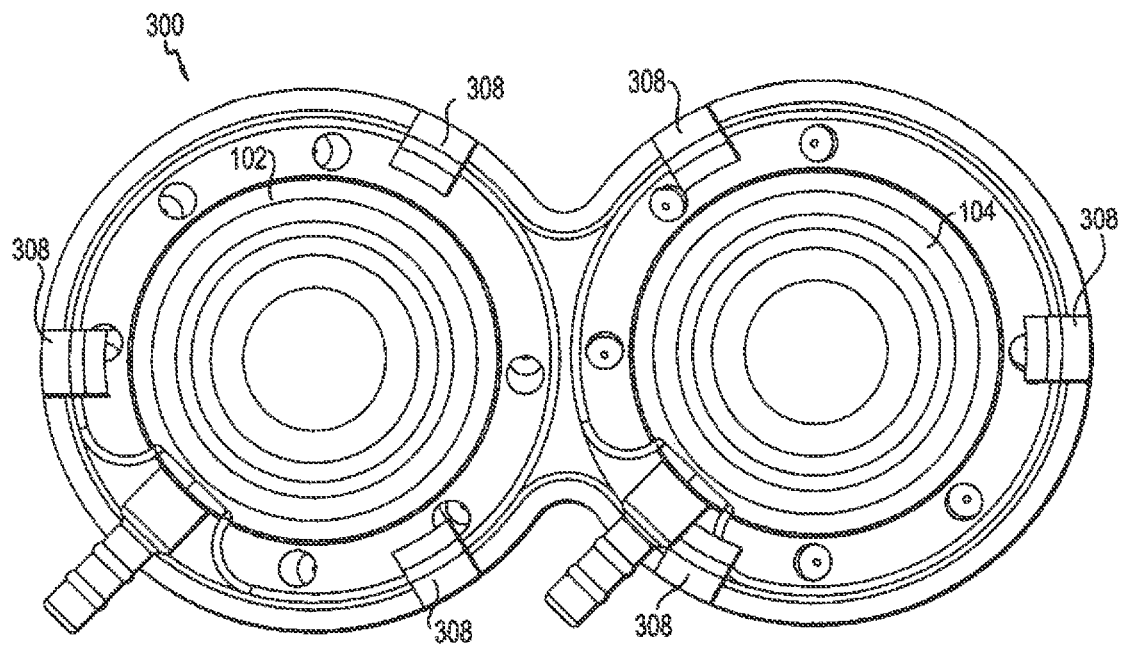
FIG. 13 is an overhead plan view of the multi-port assembly shown in FIG. 11.

As best seen in FIGS. 7, 9, and 10, the base 206 does not have a figure eight shape like base 106. Also, the base 206 does not include a bore 120 like multi-port assembly 100. Furthermore, as best seen in FIGS. 7 and 8, the multi-port assembly 200 lacks a flange 128 that joins one or more of the port couplings 208. As best seen in FIG. 8, the port couplings 208 have an extending portion 222 that extends from the base 206 and a coupling portion 224 at an end of the extending portion 222. The extending portion 222 and the coupling portion 224 may be substantially similar to the extending portion 122 and the coupling portion 124 of the multi-port assembly 100, thus a detailed description of these portions 222 and 224 are omitted. However, the port couplings 208 can omit the peg 126, as best shown in FIG. 8. In other embodiments, the base 206 can have a shape that generally resembles a figure eight, a bore 120, or a flange 128, and the port coupling 208 can include a peg 126.

Referring to FIGS. 11-14, yet another embodiment of the multi-port assembly 300 is shown. The multi-port assembly 300 includes a base 306 and three port couplings 308 that are disposed substantially equidistant apart from each other. The port couplings 308 are substantially similar to the port couplings 108 of the multi-port assembly 100, thus a detailed description thereof is omitted. Each port coupling 308 can include an extending portion 322 that extends from the base 306 and a coupling portion 324 that is disposed at an end of the extending portion 322.

Figure 14:
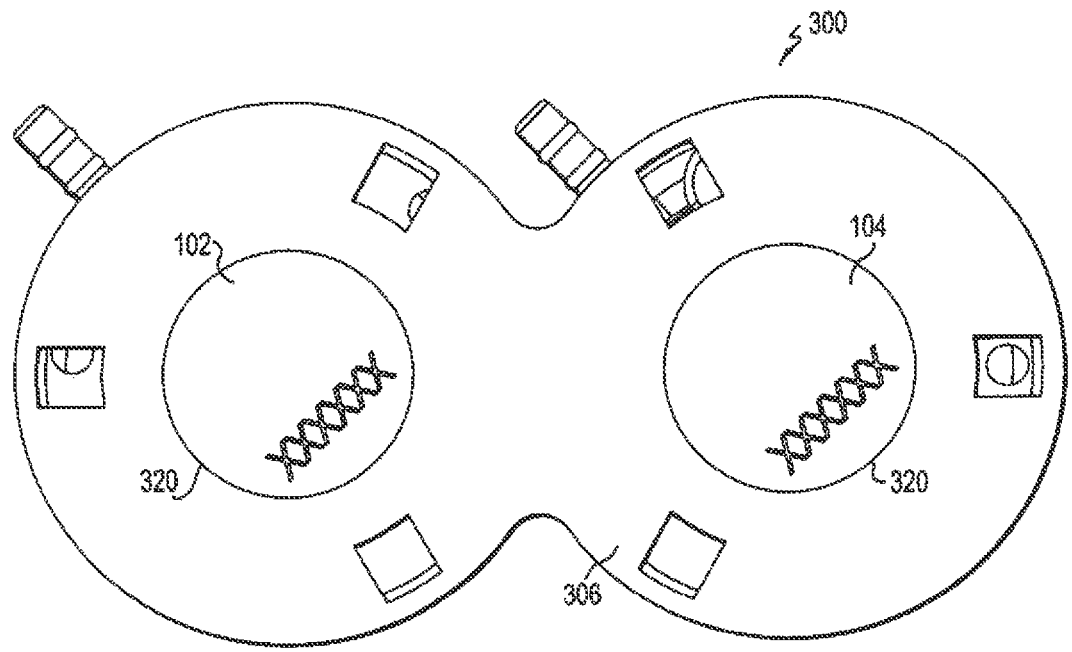
FIG. 14 is an underside plan view of the multi-port assembly shown in FIG. 11.
Figure 15:
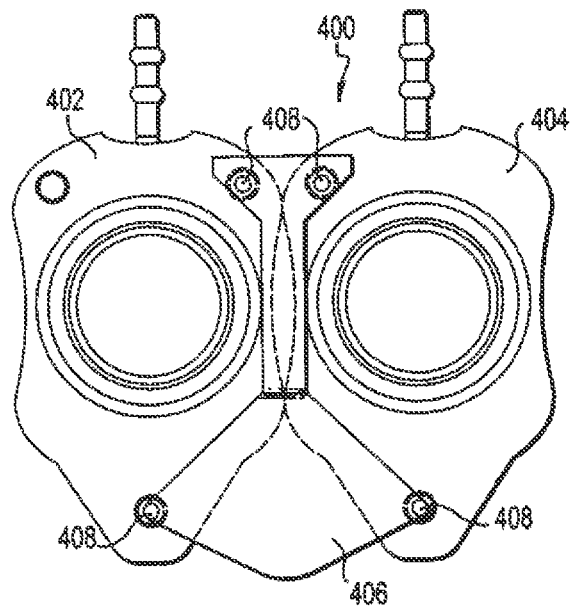
FIG. 15 is an underside plan view of a multi-port assembly in accordance with yet another embodiment of the invention.
Figure 16:
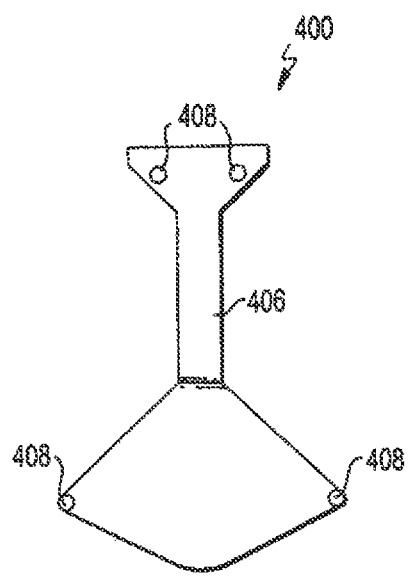
FIG. 16 is an underside plan view of the multi-port assembly shown in FIG. 15 without ports.
Figure 17:
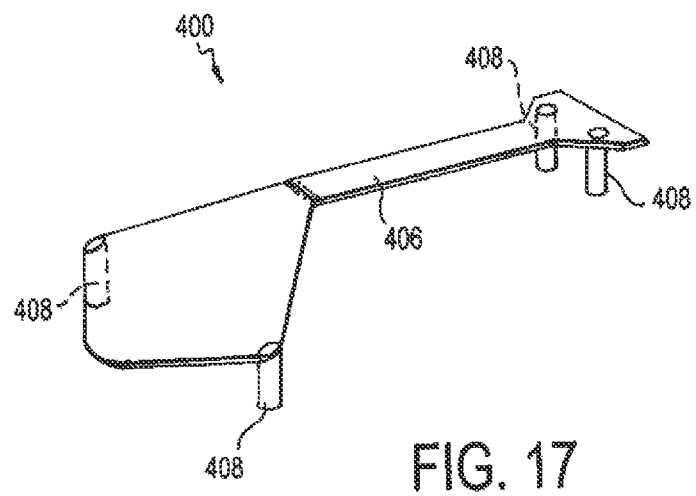
FIG. 17 is a perspective view of the multi-port assembly shown in FIG. 15.
Figure 18:
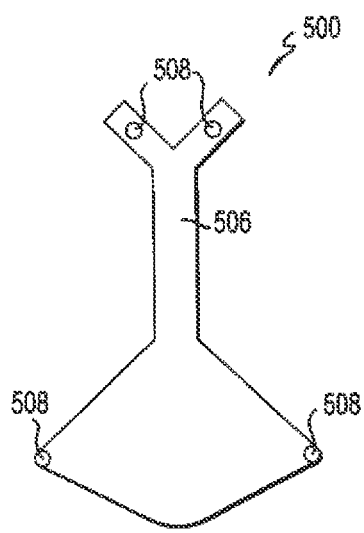
FIG. 18 is a plan view of a multi-port assembly in accordance with yet another embodiment of the invention.
Figure 19:
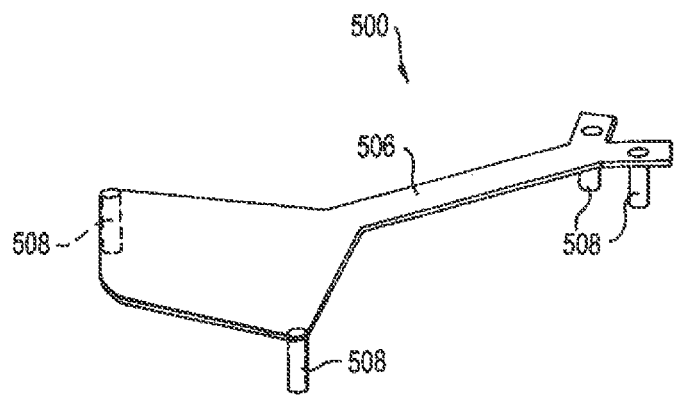
FIG. 19 is a perspective view of the multi-port assembly shown in FIG. 18.
Figure 20:
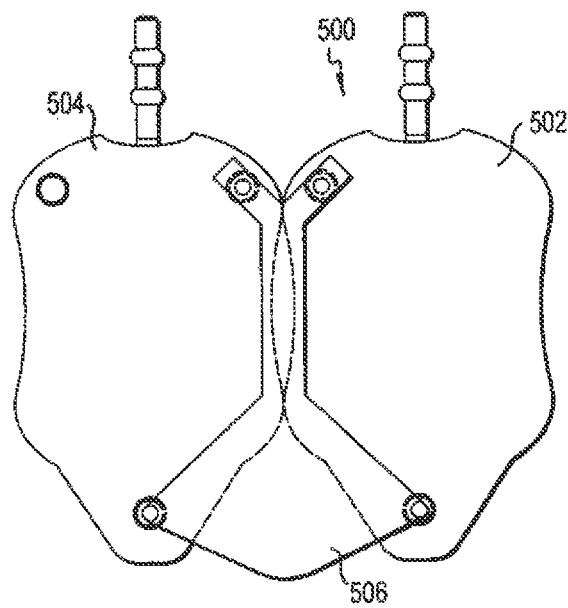
FIG. 20 is plain view of the multi-port assembly shown in FIG. 18 with ports.

The base 306 can also include a first surface 310 and a second surface 312 that are substantially similar to the first surface 110 and the second surface 112. The base 306 may also include port receiving areas (not shown) that are substantially similar to port receiving areas 114 or 116. As best shown in FIG. 14, the base 306 can also include one or more bores 320. In other embodiments, the base 306 can have a flange 128, and the port coupling 308 can include a peg 126.

Referring to FIGS. 15-20, multi-port assemblies 400 and 500 are shown. The multi-port assemblies 400 and 500 each include a base 406 and 506, respectively, that have a shape substantially conforms to portions of an outermost surface of the ports 402 and 404 or 502 and 504. The bases 406 and 506 are generally similar to base 106 of the multi-port assembly 100; however, the bases 406 and 506 have port receiving areas that receive a portion of the mating surfaces of the ports 402 and 404 or 502 and 504, instead of the entire mating surface. In the embodiment shown in FIGS. 15-17, the ports 402 and 404 are placed next to each other, and the base 406 mates with a continuous portion of surfaces of the ports 402 and 404 that are immediately adjacent to each other. In the embodiment shown in FIGS. 18-20, the ports 502 and 504 are placed next to each other, and the base 506 mates with several portions of surfaces of the ports 502 and 504 that are immediately adjacent to each other.

The base 402 or 502 can also include one or more port couplings 408 or 508 that couple the ports 402 and 404 or 502 and 504 to the base 402 or 502, respectively. The port couplings 408 or 508 are substantially similar to the port couplings 108 of the multi-port assembly 100, thus a detailed description thereof is omitted. In the embodiment shown, the port couplings 408 and 508 are pegs that are aligned with and received by suture holes in the ports 402 and 404 or 502 and 504. In an alternate embodiment, pegs on the ports 402 and 404 or 502 and 504 may be received by the base 406 or 506, respectively.

A split-type catheter (not shown) or a standard single lumen catheter can be used with the multi-port assembly 100, 200, 300, 400, or 500. The split-type catheter would couple with splittable round catheters that attach to port stems (not shown) with locking collars. The round lumens would merge into a single non-splittable catheter with internal "D" lumens. This part of the catheter would enter the venotomy. Alternatively, if the single lumen catheter is used, individual single lumen catheters can be placed adjacent to each other to couple to the ports 102 and 104, 202 and 204, 402 and 404, or 502 and 504.

While particular embodiments have been chosen to illustrate the invention, it will be understood by those skilled in the art that various changes and modifications can be made to these embodiments without departing from the scope of the invention as defined in the appended claims.

What is claimed is:

1. A multiple vascular access port assembly comprising:
    a base assembly configured to receive multiple, self-contained vascular access ports, the base assembly including:
        a first planar base surface and an opposing second planar base surface;
        multiple port receiving areas on the first base surface, each port receiving area configured to receive and removably attach to the base assembly one self-contained vascular access port, wherein each port receiving area includes:
            multiple port couplings extending from the first base surface, and along a periphery thereof, each port coupling being integral to the first base surface and including an extending portion and a coupling portion, where the extending portion extends vertically from and substantially perpendicular to the first base surface and the coupling portion extends from and substantially perpendicular to the extending portion, the coupling portion extending in a direction radially inward of the port receiving area, where an inside height of each extending portion corresponds to a thickness height of a peripheral flange of a respective, self-contained vascular access port.

2. The port assembly of claim 1, further comprising multiple, self-contained vascular access ports configured to be received by and removably attached to the base assembly, wherein each self-contained vascular access port includes a peripheral flange extending radially outwardly from a respective body thereof, and wherein a thickness height of the peripheral flange corresponds to an inside height of the respective extending portion.

3. The port assembly of claim 1, wherein each port receiving area further comprises a flange extending vertically from the first base surface, and along a periphery of the port receiving area, the flange having a height similar to an inside height of the extending portion of a port coupling, the flange configured to abut, and provide mechanical support to, an edge of the peripheral flange of the respective, self-contained vascular access port.

4. The port assembly of claim 3, wherein the flange extends around approximately one-third of the periphery of each port receiving area.

5. The port assembly of claim 3, wherein the flange joins one or more of the port couplings.

6. The port assembly of claim 1, wherein three port couplings are employed, and are disposed substantially equidistant from one another along the periphery of each port receiving area.

7. The port assembly of claim 1, wherein each port receiving area includes a knurled surface on the first base surface, the knurled surface configured to mate with a corresponding knurled surface on a bottom of each self-contained vascular access port, whereby the respective knurled surfaces lock in mating relationship upon attachment of a respective vascular access port to the base assembly.

8. The port assembly of claim 7, further comprising multiple, self-contained vascular access ports, wherein each self-contained vascular access port includes a knurled surface on a bottom thereof that corresponds to the knurled surface of a respective port receiving area, whereby the respective knurled surfaces lock in mating relationship upon attachment of a respective vascular access port to the base assembly, and wherein each self-contained vascular access port includes a peripheral flange having a thickness height corresponding to an inside height of a respective extending portion, thereby facilitating the receiving and attaching of a respective vascular access port to the base assembly.

9. The port assembly of claim 1, wherein the coupling portion of at least one port coupling of each port receiving area includes a peg perpendicularly extending therefrom to engage a surface of the peripheral flange of a respective, self-contained vascular access port, thereby providing mechanical support to the attachment of a respective vascular access port to the base assembly.

10. The port assembly of claim 1, wherein the first base surface is multi-tiered, so that a first port receiving area thereon, that receives and abuts a bottom of a first self-contained vascular access port, is disposed on a plane parallel to, but differing from, a plane of a second port receiving area thereon, that receives and abuts a bottom of a second self-contained vascular access port, wherein respective self-contained vascular access ports of different heights will be disposed with tops thereof lying on a same plane, and wherein respective self-contained vascular access ports of similar heights will be disposed with tops thereof lying on different planes.

11. A multiple vascular access port assembly comprising:
a base assembly configured to receive multiple, self-contained vascular access ports, the base assembly including:
a first planar base surface and an opposing second planar base surface;
multiple port receiving areas disposed on the first base surface, each port receiving area configured to receive and removably attach to the base assembly one self-contained vascular access port, wherein each port receiving area includes:
multiple port couplings extending from and integral to the first base surface, located along a periphery thereof, to facilitate removable attachment of a respective vascular access port to the base assembly at a respective port receiving area; and
a knurled surface on the first base surface, the knurled surface configured to mate with a corresponding knurled surface on a bottom of each self-contained vascular access port, whereby the respective knurled surfaces lock in mating relationship upon attachment of a respective vascular access port to the base assembly.

12. The port assembly of claim 11, further comprising multiple, self-contained vascular access ports, wherein each self-contained vascular access port includes a knurled surface on a bottom thereof that corresponds to the knurled surface of a respective port receiving area, whereby the respective knurled surfaces lock in mating relationship upon attachment of a respective vascular access port to the base assembly.

13. The port assembly of claim 11, wherein each port coupling includes an extending portion and a coupling portion, where the extending portion extends vertically from and substantially perpendicular to the first base surface and the coupling portion extends from and substantially perpendicular to the extending portion, the coupling portion extending in a direction radially inward of the port receiving area, where an inside height of each extending portion corresponds to a thickness height of a peripheral flange of a respective, self-contained vascular access port.

14. The port assembly of claim 13, further comprising multiple, self-contained vascular access ports, wherein each self-contained vascular access port includes a knurled surface on a bottom thereof that corresponds to the knurled surface of a respective port receiving area, whereby the respective knurled surfaces lock in mating relationship upon attachment of a respective vascular access port to the base assembly, and wherein each self-contained vascular access port includes a peripheral flange having a thickness height corresponding to an inside height of a respective extending portion, thereby facilitating the receiving and attaching of a respective vascular access port to the base assembly.

15. The port assembly of claim 13, wherein the coupling portion of at least one port coupling of each port receiving area includes a peg perpendicularly extending therefrom to engage a surface of the peripheral flange of a respective, self-contained vascular access port, thereby providing mechanical support to the attachment of a respective vascular access port to the base assembly.

16. The port assembly of claim 13, wherein each port receiving area further comprises a flange extending vertically from the first base surface, and along a periphery of the port receiving area, the flange having a height similar to an inside height of the extending portion of a coupling, flange configured to abut, and provide mechanical support to, an edge of the peripheral flange of the respective, self-contained vascular access port.

17. The port assembly of claim 16, wherein the flange joins one or more of the port couplings.

18. The port assembly of claim 11, wherein three port couplings are employed, and are disposed substantially equidistant from one another along the periphery of each port receiving area.

19. The port assembly of claim 11, wherein the first base surface is multi-tiered, so that a first port, receiving area thereon, that receives and abuts a bottom of a first self-contained vascular access port, is disposed on a plane parallel to, but differing from, a plane of a second port receiving area thereon, that receives and abuts a bottom of a second self-contained vascular access port, wherein respective self-contained vascular access ports of different heights will be disposed with tops thereof lying on a same plane, and wherein respective self-contained vascular access ports of similar heights will be disposed with tops thereof lying on different planes.

20. A multiple vascular access port assembly comprising:
a base assembly configured to receive multiple, self-contained vascular access ports, the base assembly including:
a first planar base surface and an opposing second planar base surface;
multiple port receiving areas on the first base surface, each port receiving area configured to receive and, removably attach to the base assembly one self-contained vascular access port, wherein each port receiving area includes:
multiple port couplings extending from the first base surface, and along a periphery thereof, each port coupling being integral to the first base surface and including an extending portion and a coupling portion, where the extending portion extends vertically from and substantially perpendicular to the first base surface and the coupling portion extends from and substantially perpendicular to the extending portion, the coupling portion extending in a direction radially inward of the port receiving area, where an inside height of each extending portion corresponds to a thickness height of a peripheral flange of a respective, self-contained vascular access port;

a flange extending vertically from the first base surface, and along a periphery of each port receiving area, the flange having a height similar to an inside height of the extending portion of a port coupling, the flange configured to abut, and provide mechanical support to, an edge of the peripheral flange of a respective, self-contained vascular access port; and a knurled surface on the first base surface, the knurled surface configured to mate with a corresponding knurled surface on a bottom of each self-contained vascular access port; and multiple, self-contained vascular access ports, wherein each self-contained vascular access port includes a knurled surface on a bottom thereof that corresponds to the knurled surface of a respective port receiving area, whereby the respective knurled surfaces lock in mating relationship upon attachment of a respective vascular access port to the base assembly, and wherein each self-contained vascular access port includes a peripheral flange having a thickness height corresponding to an inside height of a respective extending portion, thereby facilitating the receiving and attaching of the respective vascular access port to the base assembly.

* * * * *